United States Patent
Ramey et al.

(10) Patent No.: US 8,849,459 B2
(45) Date of Patent: Sep. 30, 2014

(54) POWER MANAGEMENT SYSTEM FOR A HANDHELD MEDICAL DEVICE

(75) Inventors: Blaine Edward Ramey, Indianapolis, IN (US); Michael C. McKee, Arlington Heights, IL (US); Michael G. Nicholas, Wheeling, IL (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 981 days.

(21) Appl. No.: 12/905,462

(22) Filed: Oct. 15, 2010

(65) Prior Publication Data

US 2012/0095312 A1   Apr. 19, 2012

(51) Int. Cl.
*G01N 33/00* (2006.01)
*A61B 5/15* (2006.01)
(Continued)

(52) U.S. Cl.
CPC ....... *A61B 5/14532* (2013.01); *A61B 5/150946* (2013.01); *A61B 5/4839* (2013.01); *A61B 5/15087* (2013.01); *A61B 2560/0443* (2013.01); *G01N 33/48785* (2013.01); *A61B 5/155* (2013.01); *A61B 5/150305* (2013.01); *A61B 5/002* (2013.01); *G01K 7/42* (2013.01); *G06F 19/3406* (2013.01); *A61B 2560/0209* (2013.01); *A61B 5/150358* (2013.01); *A61B 5/150862* (2013.01); *A61B 5/150854* (2013.01); *A61B 5/150877* (2013.01); *A61B 2560/0252* (2013.01); *A61B 5/150022* (2013.01); *A61B 5/157* (2013.01); *A61B 2560/045* (2013.01)
USPC ........................ 700/266; 422/82.12; 422/68.1

(58) Field of Classification Search
USPC ............................... 422/82.12, 68.1; 700/266
See application file for complete search history.

(56) References Cited

U.S. PATENT DOCUMENTS 5,710,404 A   1/1998   Descent
2010/0191086 A1   7/2010   Talbot et al.
(Continued)

FOREIGN PATENT DOCUMENTS

WO   WO2005000114   1/2005
WO   WO2010040090   4/2010

OTHER PUBLICATIONS

U.S. Appl. No. 12/479,212, filed Jun. 5, 2009, Ramey et al.
(Continued)

*Primary Examiner* — Sam P Siefke
(74) *Attorney, Agent, or Firm* — Roche Diagnostics Operations, Inc.

(57) ABSTRACT

A system for managing power consumption of a handheld diabetes management device and limiting effects of temperature on operations performed by the handheld diabetes management device comprises a blood glucose measuring module, a temperature sensing module, and a power management module. The blood glucose measuring module selectively measures blood glucose in a blood sample and generates a status signal indicating a status of operation of the blood glucose measuring module. The temperature sensing module senses an internal temperature of the handheld diabetes management device and estimates an ambient temperature external to the handheld diabetes management device. The power management module deactivates one or more components of the handheld diabetes management device based on the status of operation of the blood glucose measuring module when the internal temperature of the handheld diabetes management device exceeds a threshold temperature. The power management module deactivates the blood glucose measuring module when the ambient temperature is greater than a first predetermined threshold or less than a second predetermined threshold.

15 Claims, 7 Drawing Sheets

(51) Int. Cl.
*A61B 5/145* (2006.01)
*G01N 33/487* (2006.01)
*A61B 5/155* (2006.01)
*G01K 7/42* (2006.01)
*G06F 19/00* (2011.01)
*A61B 5/157* (2006.01)
*A61B 5/00* (2006.01)

(56) References Cited

U.S. PATENT DOCUMENTS

2010/0191087 A1 7/2010 Talbot et al.
2011/0054282 A1 3/2011 Nekoomaram et al.
2011/0191059 A1* 8/2011 Farrell et al. .................. 702/130

OTHER PUBLICATIONS

"i.MX233 Power Management Unit and Battery Charger"; Freescale Semiconductor, Inc.; Jul. 2009.
"System-Side Impedance Track Fuel Gauge"; Texas Instruments; Jun. 2009.
"i.MX23 Applications Processor Reference Manual"; Freescale Semiconductor; Nov. 2009.

* cited by examiner

POWER MANAGEMENT SYSTEM FOR A HANDHELD MEDICAL DEVICE

FIELD

The present disclosure relates generally to medical devices and more particularly to power management for handheld medical devices.

BACKGROUND

Medical devices are often used as diagnostic devices and/or therapeutic devices in diagnosing and/or treating medical conditions of patients. For example, a blood glucose meter is used as a diagnostic device to measure blood glucose levels of patients suffering from diabetes. An insulin infusion pump is used as a therapeutic device to administer insulin to patients suffering from diabetes.

Diabetes mellitus, often referred to as diabetes, is a chronic condition in which a person has elevated blood glucose levels that result from defects in the body's ability to produce and/or use insulin. There are three main types of diabetes. Type 1 diabetes may be autoimmune, genetic, and/or environmental and usually strikes children and young adults. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. The incidence of diabetes is increasing rapidly, and it is estimated that between 2005 and 2030, the number of deaths from diabetes will double. In the United States, nearly 24 million Americans have diabetes, and an estimated 25% of seniors age 60 and older are affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Diabetes is managed primarily by controlling the level of glucose in the bloodstream. This level complex as the level of blood glucose entering the bloodstream is dynamic and complex, and is affected by multiple factors including the amount and type of food consumed, and the amount of insulin (which mediates transport of glucose across cell membranes) in the blood. Variation of insulin in the bloodstream that controls the transport of glucose out of the bloodstream also complicates diabetes management. Blood glucose levels are also sensitive to diet and exercise, but also can be affected by sleep, stress, smoking, travel, illness, menses, and other psychological and lifestyle factors unique to individual patients. The dynamic nature of blood glucose and insulin and all other factors affecting blood glucose often require a person with diabetes to forecast blood glucose levels. Therefore, therapy in the form of insulin, oral medications, or both can be timed to maintain blood glucose levels in an appropriate range.

Management of diabetes is time-consuming for because of the need to consistently obtain reliable diagnostic information, follow prescribed therapy, and manage lifestyle on a daily basis. Diagnostic information such as blood glucose is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates, and proteins along with effects of exercise or other physiological states. The management of lifestyle factors such as body weight, diet, and exercise can significantly influence the type and effectiveness of therapy.

Management of diabetes involves large amounts of diagnostic data and prescriptive data acquired in a variety of ways: from medical devices, from personal healthcare devices, from patient-recorded logs, from laboratory tests, and from healthcare professional recommendations. Medical devices include self-monitoring blood glucose (bG) meters (BGMs), continuous glucose monitors (CGMs), ambulatory insulin infusion pumps, diabetes analysis software, and diabetes device configuration software, each of which generates and/or manages large amounts of diagnostic and prescriptive data. Personal healthcare devices include weight scales, blood pressure cuffs, exercise machines, thermometers, and weight management software. Patient recorded logs include information relating to meals, exercise, and lifestyle. Laboratory test results include HbA1C, cholesterol, triglycerides, and glucose tolerance. Healthcare professional recommendations include prescriptions, diets, test plans, and other information relating to the treatment of the patient.

There is a need for a handheld device to aggregate, manipulate, manage, present, and communicate diagnostic data and prescriptive data from medical devices, personal healthcare devices, patient recorded information, biomarker information, and recorded information in an efficient manner. The handheld device can improve the care and health of a person with diabetes so that the person with diabetes can lead a full life and reduce the risk of complications from diabetes.

Additionally, since the handheld device is battery powered, there is a need to effectively manage power consumption of the handheld device to optimize operating times between battery recharges. Specifically, there is a need to control the power consumption by selectively disabling one or more components of the handheld device based on the usage and internal temperature of the handheld device. Further, the handheld device measures blood glucose levels by performing chemical analysis of samples deposited on a strip, which is inserted into a port of the handheld device. Since chemical processes used in the chemical analysis are sensitive to temperature, there is a need to monitor internal temperature of the handheld device, estimate an ambient temperature proximate to a reaction site on the strip based on the internal temperature, and selectively disable one or more components of the handheld device based on the ambient temperature.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A system for managing power consumption of a handheld diabetes management device and limiting effects of temperature on operations performed by the handheld diabetes management device comprises a blood glucose measuring module, a temperature sensing module, and a power management module. The blood glucose measuring module selectively measures blood glucose in a blood sample and generates a status signal indicating a status of operation of the blood glucose measuring module. The temperature sensing module senses an internal temperature of the handheld diabetes management device and estimates an ambient temperature external to the handheld diabetes management device. The power management module deactivates one or more components of the handheld diabetes management device based on the status of operation of the blood glucose measuring module when the internal temperature of the handheld diabetes management device exceeds a threshold temperature. The power management module deactivates the blood glucose measuring module when the ambient temperature is greater than a first predetermined threshold or less than a second predetermined threshold Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

Figure 1:
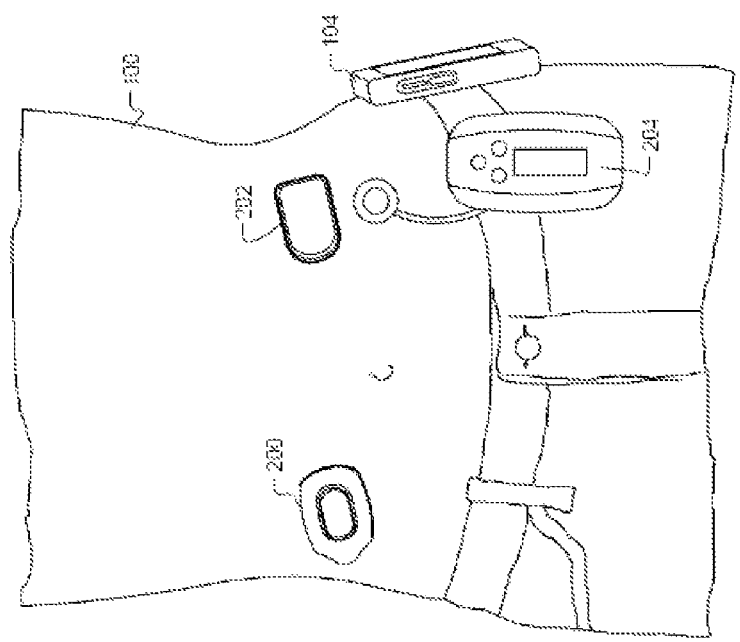
FIG. 1 shows a patient and a treating clinician.

The following description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Referring now to FIG. 1, a person 100 with diabetes and a healthcare professional 102 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 100 typically shares with the clinician 102 a variety of patient data including blood glucose measurements, continuous glucose monitor data, amounts of insulin infused, amounts of food and beverages consumed, exercise schedules, and other lifestyle information. The clinician 102 may obtain additional patient data that includes measurements of HbAlC, cholesterol levels, triglycerides, blood pressure, and weight of the patient 100. The patient data can be recorded manually or electronically on a handheld diabetes management device 104, a diabetes analysis software executed on a personal computer (PC) 106, and/or a web-based diabetes analysis site (not shown). The clinician 102 can analyze the patient data manually or electronically using the diabetes analysis software and/or the web-based diabetes analysis site. After analyzing the patient data and reviewing adherence of the patient 100 to previously prescribed therapy, the clinician 102 can decide whether to modify the therapy for the patient 100.

Figure 2:
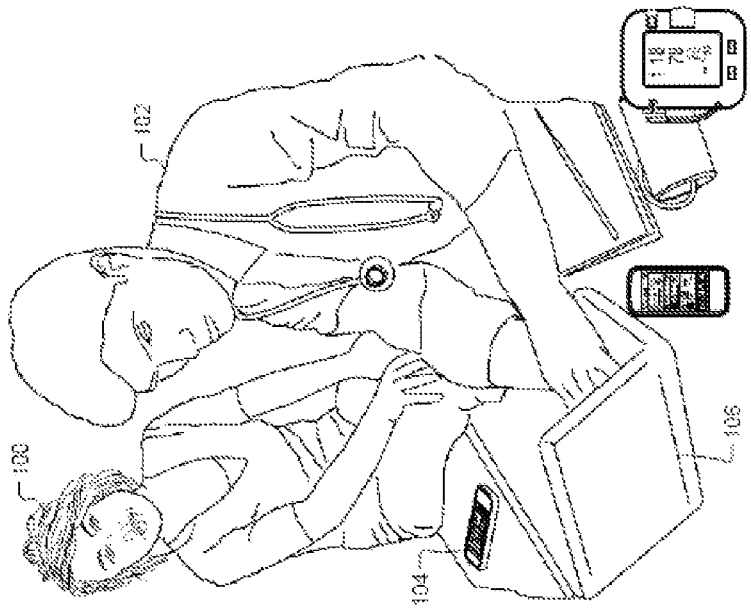
FIG. 2 shows a patient with a continuous glucose monitor (CGM), an ambulatory durable insulin infusion pump, an ambulatory non-durable insulin infusion pump, and a diabetes manger.

Referring now to FIG. 2, the patient 100 can use a continuous glucose monitor (CGM) 200, an ambulatory non-durable insulin infusion pump 202 or an ambulatory durable insulin infusion pump 204 (hereinafter insulin pump 202 or 204), and the handheld diabetes management device 104 (hereinafter the diabetes manager 104). The CGM 200 uses a subcutaneous sensor to sense and monitor the amount of glucose in interstitial fluid of the patient 100 and communicates corresponding data to the diabetes manager 104.

The diabetes manager 104 performs various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives data from the CGM 200 from which glucose levels of the patient 100 are computed. The diabetes manager 104 transmits instructions to the insulin pump 202 or 204, which delivers insulin to the patient 100. Insulin can be delivered in a scheduled manner in the form of a basal dose, which maintains a predetermined insulin dose to the patient 100. Additionally, insulin can be delivered in the form of a bolus dose, which raises the amount of insulin delivered to the patient 100 by a predetermined amount.

Figure 3:
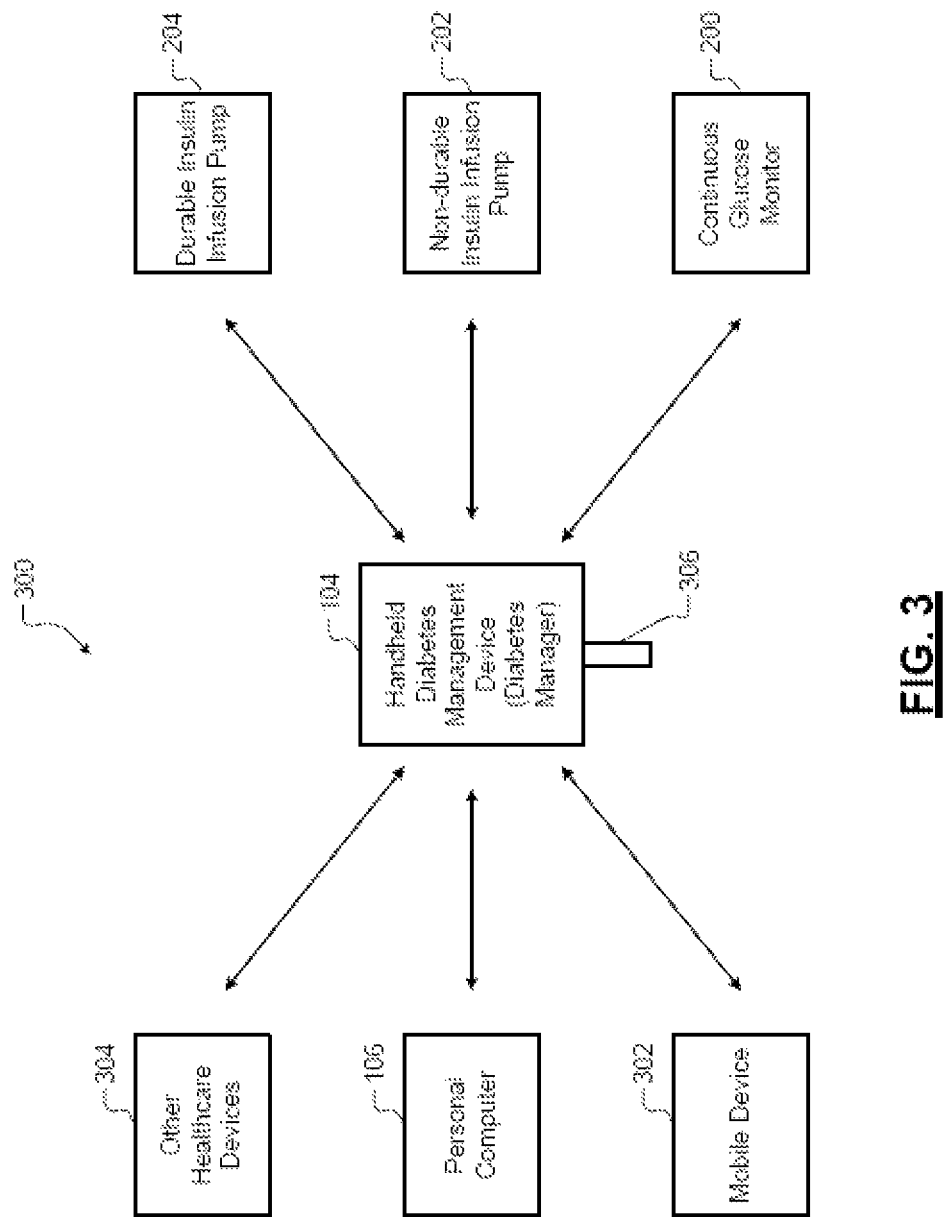
FIG. 3 shows a diabetes management system used by patients and clinicians to manage diabetes.

Referring now to FIG. 3, a diabetes management system 300 used by the patient 100 and the clinician 102 includes one or more of the following devices: the diabetes manager 104, the continuous glucose monitor (CGM) 200, the insulin pump 202 or 204, a mobile device 302, the PC 106 with the diabetes analysis software, and other healthcare devices 304. The diabetes manager 104 is configured as a system hub and communicates with the devices of the diabetes management system 300. Alternatively, the mobile device 302 can serve as the system hub. Communication between the devices in the diabetes management system 300 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 100 and clinician 102 to exchange information.

The diabetes manager 104 can receive glucose readings from one or more sources (e.g., from the CGM 200). The CGM 200 continuously monitors the glucose level of the patient 100. The CGM 200 periodically communicates data to the diabetes manager 104 from which the diabetes manager 104 computes glucose levels of the patient. The diabetes manager 104 and the CGM 200 communicate wirelessly using a proprietary wireless protocol. Throughout the present disclosure, Gazell wireless protocol developed by Nordic Semiconductor, Inc. is used as an example only. Any other suitable wireless protocol can be used instead. The Gazell wireless protocol is described in nRF24LE1 Ultra-low Power Wireless System On-Chip Solution, Product Specification v1.4, which is incorporated herein by reference in its entirety.

Additionally, the diabetes manager 104 includes a blood glucose meter (BGM) and a port that communicates with the BGM (not shown). The port can receive a blood glucose measurement strip 306. The patient 100 deposits a sample of blood on the blood glucose measurement strip 306. The BGM analyzes the sample and measures the blood glucose level in the sample. The blood glucose measured from the sample and/or the blood glucose level read by the CGM 200 can be used to determine the amount of insulin to be administered to the patient 100.

The diabetes manager 104 communicates with the insulin pump 202 or 204. The insulin pump 202 or 204 can be configured to receive instructions from the diabetes manager 104 to deliver a predetermined amount of insulin to the patient 100. Additionally, the insulin pump 202 or 204 can receive other information including meal and/or exercise schedules of the patient 100. The insulin pump 202 or 204 can determine the amount of insulin to administer based on the additional information.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication protocol such as Bluetooth. Other wireless or wireline communication protocols can also be used.

In addition, the diabetes manager 104 can communicate with the other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 may use communication protocols compliant with ISO/IEEE 11073 extended using guidelines from Continual® Health Alliance. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using Bluetooth, USB, or other interfaces. A diabetes management software running on the PC 106 includes an analyzer-configurator that stores configuration information of the devices of the diabetes management system 300. The configurator has a database to store configuration information of the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth. The mobile device 302 may include a cellular phone, a pager, or a personal digital assistant (PDA). The diabetes manager 104 can send messages to an external network through the mobile device 302. The mobile device 302 can transmit messages to the external network upon receiving requests from the diabetes manager 104.

Figure 4:
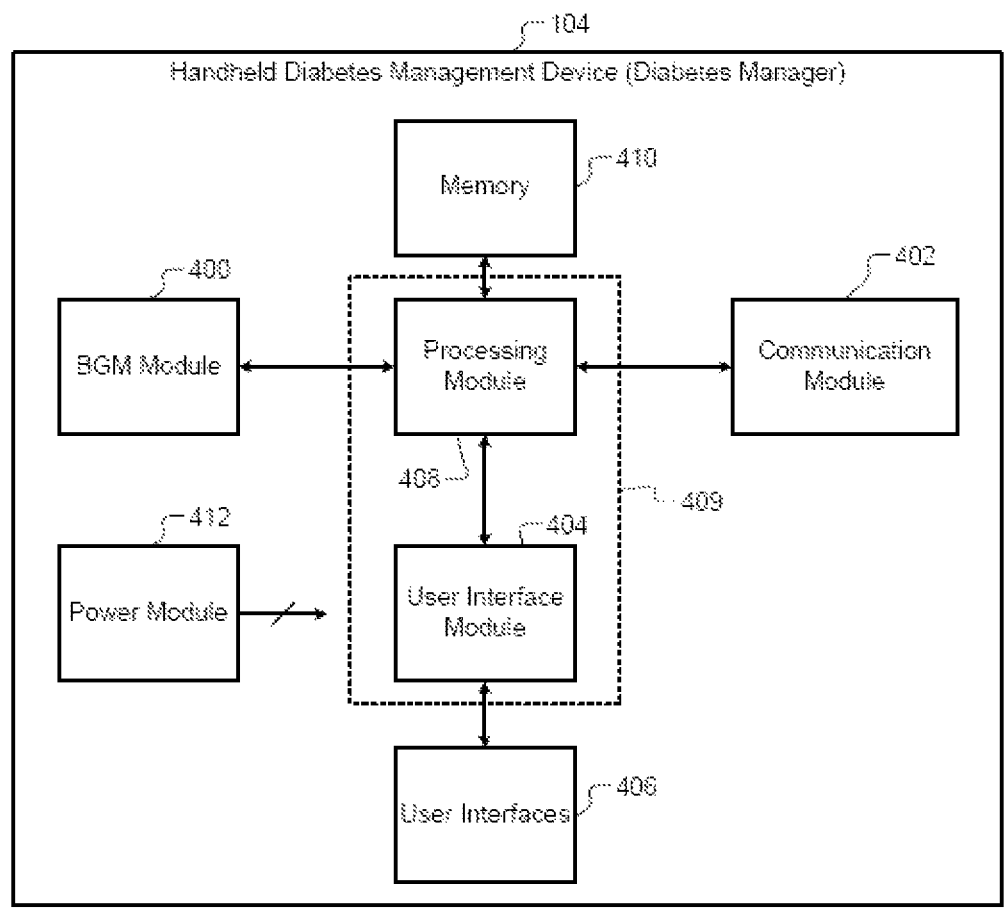
FIG. 4 is a functional block diagram of a diabetes manager.

Referring now to FIG. 4, the diabetes manager 104 comprises a blood glucose measuring (BGM) module 400, a communication module 402, a user interface module 404, user interfaces 406, a processing module 408, memory 410, and a power module 412. The user interface module 404 and the processing module 408 can be implemented by an application processing module 409. The BGM module 400 includes a blood glucose measuring engine that analyzes samples provided by the patient 100 on the blood glucose measurement strip 306 and that measures the amount of blood glucose in the samples. The communication module 402 includes multiple radios that communicate with different devices of the diabetes management system 300. The user interface module 404 interfaces the diabetes manager 104 to various user interfaces 406 that the patient 100 can use to interact with the diabetes manager 104. For example, the user interfaces 406 can include keys, switches, a display, a speaker, a microphone, a secure digital (SD) card port, a USB port, etc. (not shown).

The processing module 408 processes data received from the BGM module 400, the communication module 402, and the user interface module 404. The processing module 408 uses memory 410 for processing and storing data. The memory 410 can include volatile and nonvolatile memory. The processing module 408 outputs data to and receives data from the user interfaces 406 via the user interface module 404. The processing module 408 outputs data to and receives data from the devices of the diabetes management system 300 via the communication module 402. The power module 412 supplies power to the components of the diabetes manager 104. The power module 412 includes a rechargeable battery. The battery can be recharged using an adapter that plugs into a wall outlet. The battery can also be charged via the USB port of the diabetes manager 104.

Figure 5:
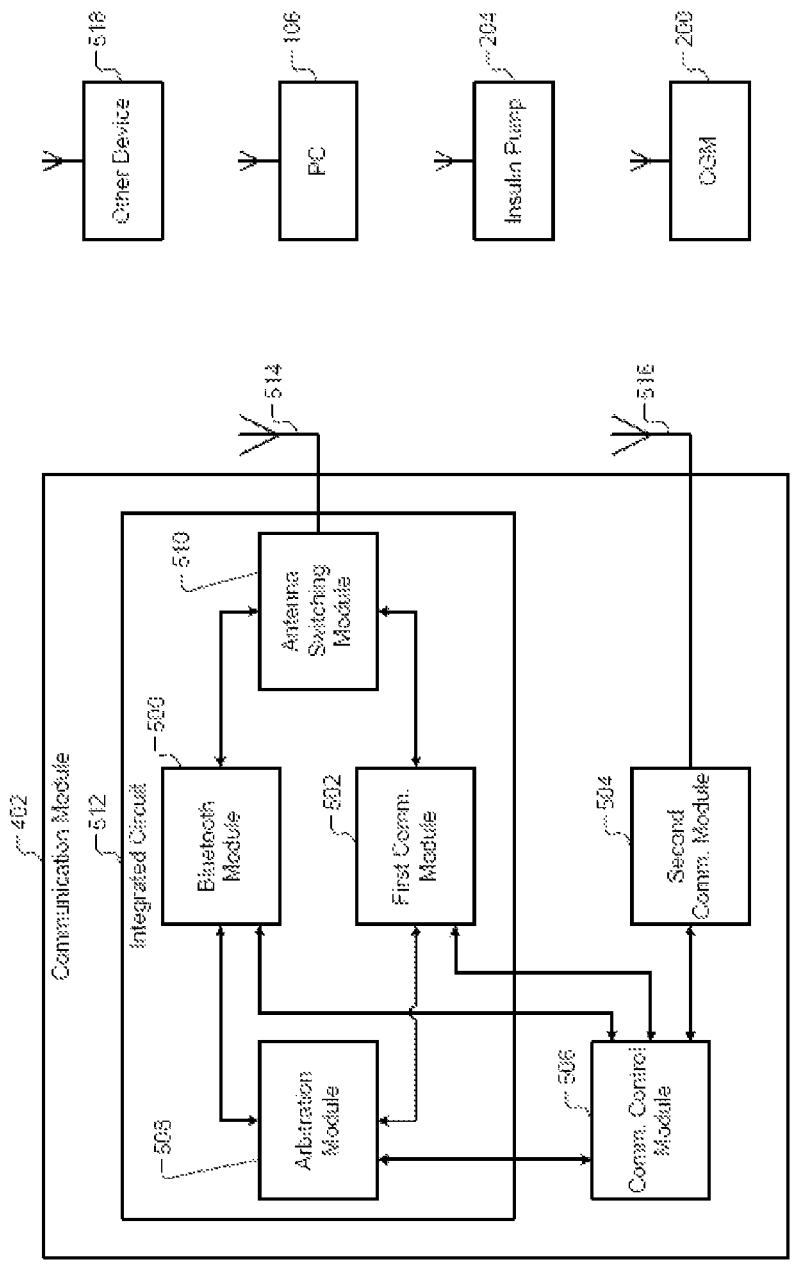
FIG. 5 is a functional block diagram of a communication module used by the diabetes manager of FIG. 4.

Referring now to FIG. 5, the communication module 402 comprises a Bluetooth module 500, a first communication module 502, a second communication module 504, a communication control module 506, an arbitration module 508, and an antenna switching module 510. The Bluetooth module 500 and the first communication module 502 are integrated into an integrated circuit (IC) 512. The Bluetooth module 500 and the first communication module 502 communicate in a 2.4 GHz frequency band (industrial, scientific, and medical or ISM band). The Bluetooth module 500 and the first communication module 502 share a first antenna 514. The second communication module 504 may operate in the ISM band or in a different frequency band and uses a second antenna 516.

Specifically, the Bluetooth module 500 communicates in the ISM band with the insulin pump 204 or the PC 106 via the first antenna 514 using the Bluetooth protocol. The first communication module 502 communicates in the ISM band with the CGM 200 via the first antenna 514 using the Gazell protocol. The second communication module 504 communicates with other device 518 using a wireless communication protocol different than Bluetooth and Gazell protocols. Throughout the present disclosure, the insulin pump 204, the PC 106, the CGM 200, and related priorities are used as examples only. Additionally or alternatively, the Bluetooth module 500 and the first and second communication modules 502 and 504 can communicate with other devices, and the other devices can have different priorities.

The communication control module 506 controls communication of the diabetes manager 104 with the other devices in the diabetes management system 300 via the Bluetooth module 500 and the first and second communication modules 502 and 504. The arbitration module 508 arbitrates priority between the Bluetooth module 500 and the first communication module 502 when communication via the Bluetooth module 500 and the first communication module 502 is attempted concurrently. The antenna switching module 510 switches the connection of the first antenna 514 between the Bluetooth module 500 and the first communication module 502 depending on whether the Bluetooth module 500 or the first communication module 502 is granted priority.

Figure 6:
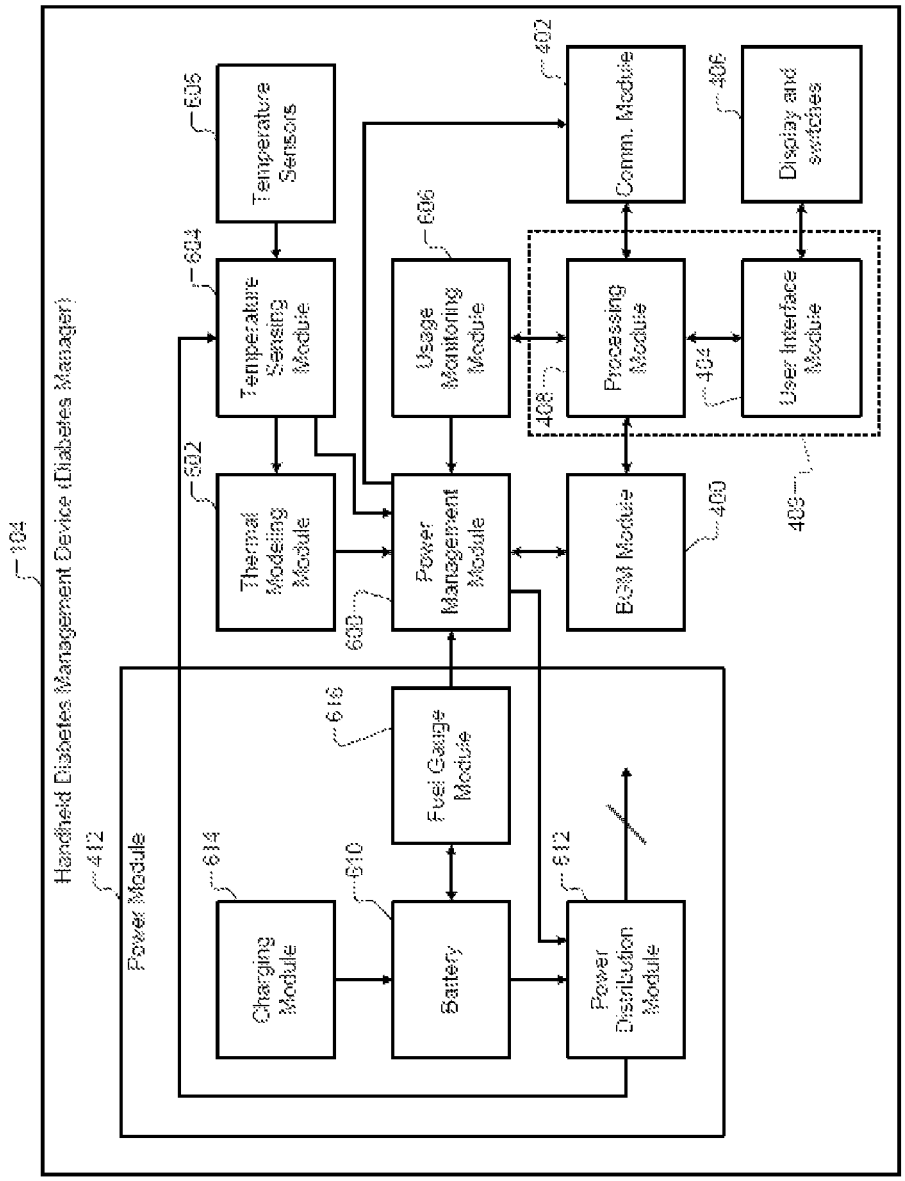
FIG. 6 is a detailed functional block diagram of the diabetes manager of FIG. 4.

Referring now to FIG. 6, a detailed functional block diagram of the diabetes manager 104 is shown. Elements of the diabetes manager 104 that are described above are not described again. In addition to these elements, the diabetes manager 104 includes a power management module 600, a thermal modeling module 602, a temperature sensing module 604, a plurality of temperature sensors 605, and a usage monitoring module 606. Further, the power module 412 includes a rechargeable battery 610, a power distribution module 612, a charging module 614, and a fuel gauge module 616. The power distribution module 612 selectively converts and distributes the power from the battery 610 to the components of the diabetes manager 104. The fuel gauge module 616 determines the remaining capacity of the battery 610. The charging module 614 charges the battery 610.

The power management module 600 controls power consumption of the diabetes manager 104 based on inputs received from the thermal modeling module 602, the temperature sensing module 604, the temperature sensors 605, the usage monitoring module 606, and the power module 412. Based on these inputs, the power management module 600 outputs power control signals to the power distribution module 612. The power distribution module 612 supplies power to the components of the diabetes manager 104 based on the power control signals.

More specifically, the power distribution module 612 receives power from the battery 610 and generates different voltages and currents suitable for the different components of the diabetes manager 104. The power distribution module 612 outputs the voltages and currents (collectively power) to the components according to the power control signals received from the power management module 600. Depending on the power control signals, the power distribution module 612 can supply full power, no power, or standby power to one or more components. The components are activated when full power is supplied and deactivated when no power or standby power is supplied. For a plurality of standby modes, a plurality of intersecting sets of components may be activated to satisfy a plurality of device use cases.

Additionally, depending on the power control signals, the power distribution module 612 can control frequencies of clock signals supplied to the components to conserve power. For example, a frequency of a clock signal supplied to a component when standby power is supplied to the component is less than the frequency when full power is supplied to the component. Use of clock signals having lower than normal frequencies requires less power than use of clock signals having normal clock frequencies, and this relationship scales linearly.

The temperature sensors 605 are located at different locations in the diabetes manager 104. The temperature sensors 605 sense and output temperatures at the different locations to the temperature sensing module 604. The temperature sensing module 604 outputs the temperatures to the thermal modeling module 602. The thermal modeling module 602 processes the temperatures using a thermal model. Based on the processing, the thermal modeling module 602 estimates an internal temperature of the diabetes manager 104, a rate of change of the internal temperature, and an ambient temperature proximate to the blood glucose measurement strip 306. The thermal model is described in U.S. patent application Ser. No. 12/479,212, filed Jun. 5, 2009, which is incorporated herein by reference in its entirety. The thermal model is also described below.

The temperature sensing module 604 can also estimate the internal temperature and the rate of change of the internal temperature based on the amount of power supplied by the power distribution module 612 to one or more components of the diabetes manager 104. Specifically, the internal temperature of the diabetes manager 104 and the rate of change of the internal temperature are directly proportional to the amount of power consumed by the components of the diabetes manager 104. The power distribution module 612 can provide data to the temperature sensing module 604 indicating when and how long a component is activated and deactivated. Accordingly, the temperature sensing module 604 can estimate the amount of heat generated by the component. Based on the estimates of heat generated by the components, the temperature sensing module 604 can estimate the internal temperature and the rate of change of the internal temperature of the diabetes manager 104.

The usage monitoring module 606 monitors the usage of the diabetes manager 104. For example, the usage can include, but is not limited to, one or more of these operations of the diabetes manager 104: blood glucose measurement, interactions with the patient 100 (e.g., receiving inputs, displaying data, generating alerts/alarms, etc.), communications with one or more devices external to the diabetes manager 104 (e.g., receiving diagnostic data from the CGM 200 or updates from the PC 106, transmitting instructions to the insulin pump 204, etc.), and so on. The usage monitoring module 606 outputs the usage data to the power management module 600. The usage data can also include data regarding planned or scheduled usage of one or more components of the diabetes manager 104 (e.g., blood glucose measurement).

The power management module 600 uses the usage data and the remaining capacity of the battery 610 generated by the fuel gauge module 616 to determine whether to activate or deactivate one or more components of the diabetes manager 104. For example, when the remaining capacity of the battery is less than a predetermined threshold, the power management module 600 generates the power control signals to deactivate components that consume large amount of power (e.g., the communication module 402). Additionally, based on the usage data, the power management module 600 can deactivate components that are idle (e.g., display) and/or that are not scheduled to be used for a predetermined period of time (e.g., the BGM module 400).

The blood glucose measurements performed by the BGM module 400 involve chemical analysis of the sample provided by the patient 100 on a reaction site of the blood glucose measurement strip 306. The chemical processes are sensitive to temperature. Since the port that receives the blood glucose measurement strip 306 is proximate to the components of the diabetes manager 104, the chemical processes at the reaction site can be affected by the internal temperature of the diabetes manager 104. Accordingly, the blood glucose levels measured by the BGM module 400 can be skewed by the internal temperature of the diabetes manager 104.

In some blood glucose measurement strips, the chemical processes at the reaction site may be relatively insensitive to the internal temperature of the diabetes manager 104. However, the accuracy of the blood glucose levels measured by the BGM module 400 is characterized over a specified temperature range (e.g., 6° C. to 44° C.). The ambient temperature at the reaction site can be different than the internal temperature of the diabetes manager 104 due to low thermal conductivity of the blood glucose measurement strip 306. Accordingly, if the internal temperature of the diabetes manager 104 is near 44° C. and is greater than the ambient temperature at the blood glucose measurement strip 306, the BGM module 400 may be prevented from measuring the blood glucose level (false positive). Conversely, if the ambient temperature at the blood glucose measurement strip 306 is near 6° C. and is less than the internal temperature of the diabetes manager 104, the BGM module 400 may be permitted to measure the blood glucose level (false negative). These problems can be alleviated as follows.

The thermal modeling module 602 estimates the ambient temperature proximate to the reaction site based on the internal temperature of the diabetes manager 104. The power management module 600 deactivates one or more components of the diabetes manager 104 when the ambient temperature, the internal temperature, and/or the rate of change of internal temperature are greater than a predetermined threshold. The BGM module 400 generates a status signal indicating whether a measurement is scheduled in a predetermined time or whether a measurement is in progress. For example, the status signal can indicate whether a measurement is scheduled at a particular time of the day. The status signal can also indicate a present status of the BGM module 400 (e.g., whether the BGM module 400 is performing a measurement or is idle). Based on the information conveyed by the status signal, the power management module 600 can deactivate one or more components of the diabetes manager 104 before or while the BGM module 400 measures blood glucose levels. For example, the power management module 600 can deactivate at least one or all of the communication modules 500, 502, and 504 before or while the BGM module 400 measures blood glucose levels.

Further, the diabetes manager 104 can be configured to partially operate during charging of the battery 610 depending on the state of charge of the battery 610. For example, when the state of charge is greater than a first predetermined threshold, one or more of the communication modules 500, 502, and 504 may be used to communicate with corresponding external devices (e.g., the insulin pump 204, the PC 106, and/or the CGM 200). When the state of charge is greater than a second predetermined threshold, one or more of the user interfaces can be operated. For example, the display can operate at full brightness; the speaker can operate at full volume; and so on. When the state of charge is greater than a third predetermined threshold, the BGM module 400 can be operated, and so on. These are only examples of sequences in which components of the diabetes manager 104 can be operated during charging. Other sequences can be used.

The internal temperature of the diabetes manager 104 can rise during charging of the battery 610 and can remain high for a period of time after charging is complete. This could ordinarily skew and therefore prevent blood glucose measurements of the BGM module 400. The power management module 600, however, deactivates one or more components of the diabetes manager 104 based on inputs received from the thermal modeling module 602, temperature sensing module 604, the temperature sensors 605, and the usage monitoring module 606 during charging of the battery 610.

Accordingly, the internal temperature of the diabetes manager 104 does not rise to a value that can skew the blood glucose measurements of the BGM module 400. Further, the thermal modeling module 602 estimates the ambient temperature proximate to the reaction site based on the internal temperature, and the BGM module 400 adjusts blood glucose measurements based on the estimated ambient temperature. Alternatively, based on the estimated ambient temperature, the power management module 600 can determine whether to permit the BGM module 400 to measure blood glucose. Thus, the BGM module 400 can reliably measure blood glucose levels during charging of the battery 610 despite a rise in the internal temperature of the diabetes manager 104.

The power management module 600 can also forecast remaining operating time of the diabetes manager 104 based on the remaining capacity of the battery 610 received from the fuel gauge module 616 and usage data received from the usage monitoring module 606. The power management module 600 can use the forecast to select components of the diabetes manager 104 to deactivate. Further, the power management module 600 can determine when and how long to deactivate the selected components. In some implementations, the power management module 600 can also determine an order in which the selected components can be deactivated and reactivated. Thus, the power management module 600 can use the forecast to prioritize and schedule power that can be supplied to one or more components of the diabetes manager 104.

For example, based on the forecast, the power management module 600 can output control signals to the arbitration module 508, which can arbitrate priority between the Bluetooth module 500 and the first communication module 502 based on the control signals. When the control signals indicate that the remaining capacity of the battery 610 is less than a predetermined threshold, the arbitration module 508 can deny permission to one or more of the communication modules 500, 502, and 504 that consume more power and grant priority to one of the communication modules 500, 502, and 504 that consumes less power.

For example, the CGM 200 monitors blood glucose more frequently than the insulin pump 204 delivers insulin. Further, the first communication module 502 communicates with the CGM 200 more frequently than the frequency at which the Bluetooth module 500 communicates with the insulin pump 204. Further, the Bluetooth module 500 may not communicate frequently with other devices such as the PC 106. Consequently, the first communication module 502 consumes more power than the Bluetooth module 500. Accordingly, the power management module 600 can deactivate the first communication module 502 before deactivating the Bluetooth module 500.

Further, when the control signals indicate that the remaining capacity of the battery 610 is less than a predetermined threshold and an operation such as blood glucose measurement is scheduled to be performed, the power management module 600 can reduce output levels of one or more of the user interfaces 406 to conserve power until the battery 610 is recharged. For example, brightness of the display and/or volume of the speaker can be limited to less than a predetermined threshold until the battery 610 is recharged.

Figure 7A:
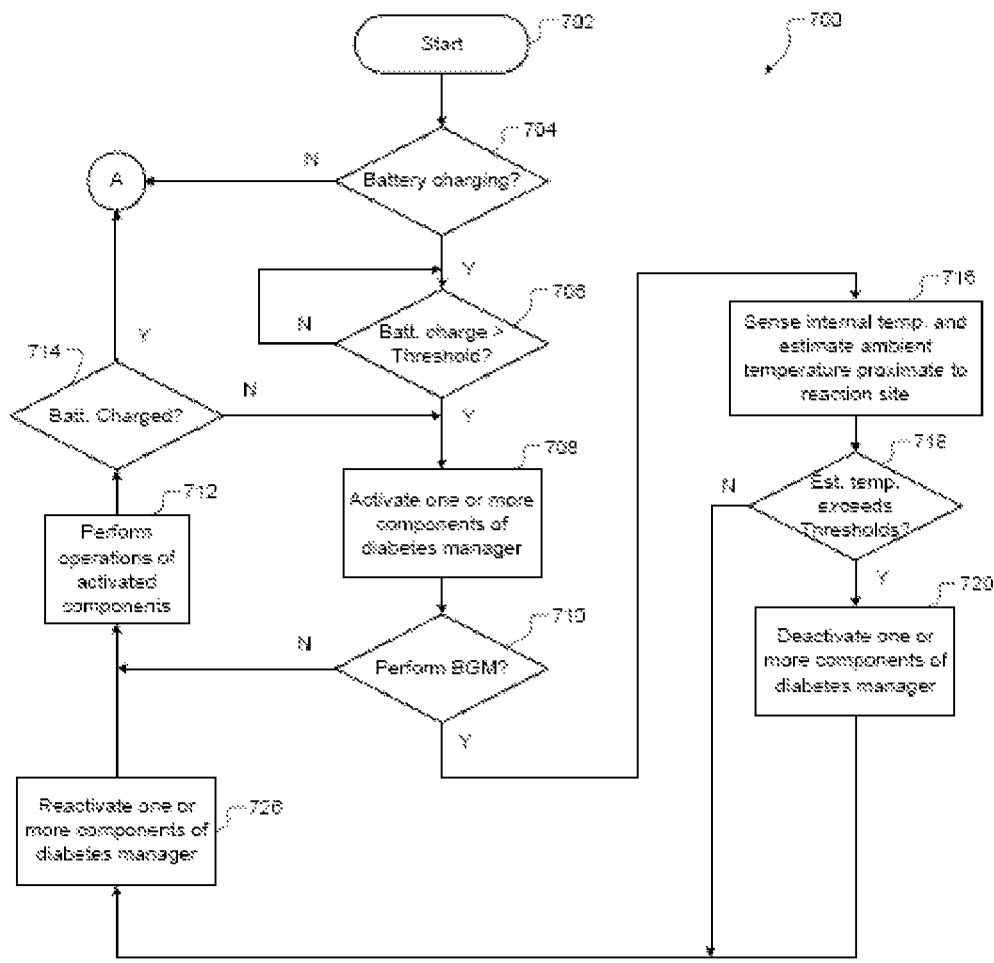
FIGS. 7A and 7B depict a flowchart of a method for managing power consumption of the diabetes manager and limiting effects of temperature on operations performed by the diabetes manager of FIG. 4.
Figure 7B:
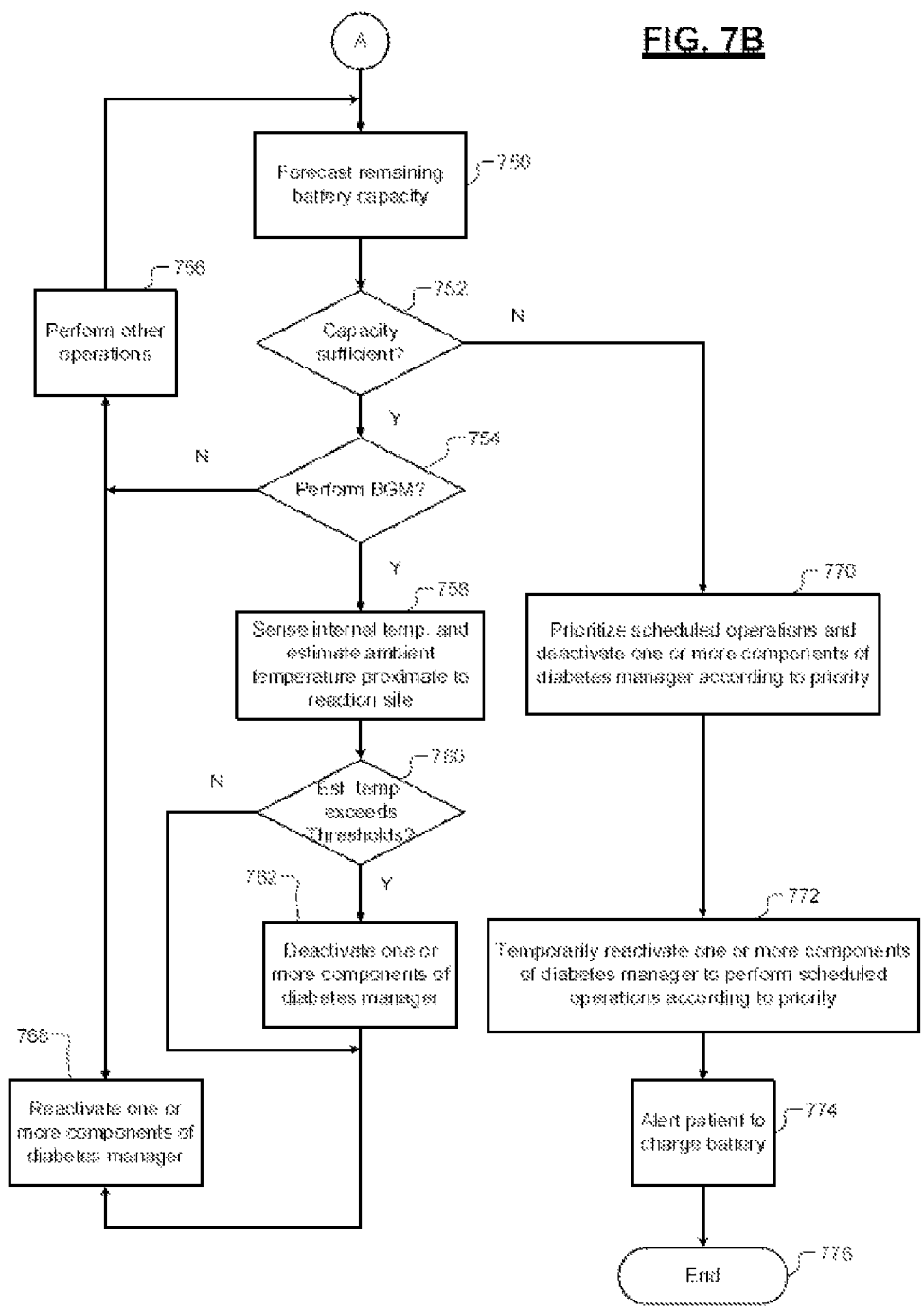

Referring now to FIGS. 7A and 7B, in an exemplary implementation, the power management module 600 performs a method 700. In FIG. 7A, control begins at 702. At 704, control determines if the battery 610 is charging. If the battery 610 is not charging, control goes to 750 (see FIG. 7B). If the battery 610 is charging, at 706, control determines if the state of charge of the battery 610 is greater than a predetermined threshold, which indicates that the battery 610 has sufficient charge to supply power to one or more components of the diabetes manager 104. Control waits until the state of charge of the battery 610 is greater than a predetermined threshold. When the state of charge of the battery 610 is greater than a predetermined threshold, at 708, control activates one or more components of the diabetes manager 104.

At 710, control determines if a blood glucose measurement (BGM) is to be performed. If a BGM is not to be performed, at 712, control performs operations of activated components. At 714, control determines if the battery 610 is charged. If the battery 610 is charged, control goes to 750 (see FIG. 7B). If the battery 610 is not charged, control returns to 708.

At 716, if a BGM is to be performed, control senses the internal temperature of the diabetes manager 104 and uses the thermal model to estimate the external temperature. At 718, control determines if the estimated external temperature is greater than a first predetermined threshold or less than a second predetermined threshold. If either case is true, at 720, control deactivates one or more components of the diabetes manager 104. Thereafter, or if the estimated external temperature does not exceed the predetermined thresholds, at 726, control reactivates one or more deactivated components, and control returns to 712. In some implementations, instead of waiting for the temperature to return to an acceptable temperature range, the processing module 408 can output a message to the patient 100 that the temperature is outside the acceptable temperature range, and testing is disallowed.

In FIG. 7B, at 750, control forecasts the remaining battery capacity as described above. At 752, control determines if the remaining battery capacity is sufficient to perform scheduled operations. If the remaining battery capacity is sufficient to perform scheduled operations, at 754, control determines if a blood glucose measurement (BGM) is to be performed. If a BGM is not to be performed, at 756, control performs other scheduled operations of the diabetes manager 104, and control returns to 750.

At 758, if a BGM is to be performed, control senses the internal temperature of the diabetes manager 104 and uses the thermal model to estimate the external temperature. At 760, control determines if the estimated external temperature is greater than a first predetermined threshold or less than a second predetermined threshold. If either case is true, at 762, control deactivates one or more components of the diabetes manager 104. Thereafter, or if the estimated external temperature does not exceed the predetermined thresholds, at 768, control reactivates one or more deactivated components, and control returns to 756. In some implementations, instead of waiting for the temperature to return to an acceptable temperature range, the processing module 408 can output a message to the patient 100 that the temperature is outside the acceptable temperature range, and testing is disallowed.

At 770, if the remaining battery capacity is insufficient (e.g., less than a predetermined threshold) to perform scheduled operations, control prioritizes scheduled operations of the diabetes manager 104 and deactivates one or more components of the diabetes manager 104 according to the priority. Control also limits capabilities of one or more user interfaces 406 (e.g., display, speaker, etc.) of the diabetes manager 104. At 772, control temporarily reactivates one or more deactivated components to perform the scheduled operations according to the priority, and deactivates the components after the scheduled operations are completed. At 774, control alerts the patient 100 to charge the battery 610, and control ends at 776.

In summary, a system for managing the power consumption of diabetes manager 104 and limiting effects of temperature on operations performed by the diabetes manager 104 includes the BGM module 400, the temperature sensing module 604, and the power management module 600. The BGM module 400 selectively measures blood glucose in a blood sample and generates a status signal indicating a status of operation of the BGM module 400. The temperature sensing module 604 senses the internal temperature of the diabetes manager 104. The power management module 60 deactivates one or more components of the diabetes manager 104 based on the status of operation of the BGM module 400 when the internal temperature of the diabetes manager 104 exceeds a threshold temperature.

In an alternative embodiment, the system includes a temperature sensor (e.g., 605) that senses the internal temperature of the diabetes manager 104 and a port that externally receives a removable measurement strip (e.g., 306) having a reaction site for receiving a blood sample. The system further includes the thermal modeling module 602 and the power management module 600. The thermal modeling module 602 uses a thermal model to estimate the ambient temperature proximate to the reaction site based on the internal temperature. The power management module 600 deactivates one or more components of the diabetes manager 104 when the ambient temperature proximate to the reaction site is greater than a first threshold temperature or is less than a second threshold temperature.

Stated generally, a system for managing power consumption of a handheld medical device (e.g., 104) and limiting effects of temperature on operations performed by the handheld medical device includes a temperature sensor (e.g., 605), a port, a thermal modeling module (e.g., 602), and a power management module (e.g., 600). The temperature sensor senses an internal temperature of the medical device. The port externally receives a removable measurement strip having a reaction site for receiving a sample of a substance for measuring a health parameter of a patient. The thermal modeling module uses a thermal model to estimate an ambient temperature proximate to the reaction site based on the internal temperature. The power management module deactivates one or more components of the medical device when the ambient temperature proximate to the reaction site is greater than a first threshold temperature or is less than a second threshold temperature.

The thermal model utilized by the thermal modeling module 602 is now described. The thermal model provides a method for estimation of the temperature at a blood glucose (bG) test strip reaction site when the test strip (e.g., the glucose measurement strip 306) may be at a different temperature than the bG measurement electronic circuitry (e.g., the BGM module 400 or the diabetes manager 104). The readings from the temperature sensor (e.g., the temperature sensors 405) in the bG measurement circuitry are used by a temperature estimation algorithm to estimate the temperature at the bG test strip reaction site. It is important to know the temperature at the reaction site in order to avoid unwarranted over-temperature lockout conditions, or to ignore valid under-temperature lock-out conditions, that would prevent proper use of the bG meter. Since all but the base of the bG test strip is exposed to the ambient air, the reaction site temperature closely follows the ambient air temperature. Studies have confirmed that the test strip has low thermal conductivity, so the internal temperature of the BGM module may differ from the temperature of the reaction site on the test strip.

In its simplest form, the algorithm uses a reading from a temperature sensor as the estimate of the reaction site temperature. If the reading is changing at a rate that exceeds a specified threshold, the temperature estimation algorithm may obtain an improved estimate of the ambient air temperature, and hence the reaction site temperature, by amplifying those changes in the temperature sensor reading and formulating a new prediction based on a static thermal model of the bG measurement device.

The reading from the sensor can, however, change not due to changes in the ambient air, but rather due to the internal heating of electronic components inside the device containing the bG circuitry (e.g., the diabetes manager 104). For example, consider the case of bG measurement circuitry installed in a cell phone. Due to the high operating temperature of circuitry inside the cell phone, the temperature readings from the temperature sensor may be unduly elevated. Furthermore, the internal heat generation may vary depending on how the cell phone is being used. Accurate temperature estimation must continue even when the thermal characteristics of the device change with specific usage.

The thermal model provides a method for estimating the temperature elevation due to any number of heat sources of arbitrary strength and arbitrary duration. Once the total expected temperature elevation has been determined, then this quantity can be subtracted from the temperature sensor reading to furnish a corrected temperature reading upon which an accurate ambient temperature prediction can be based. An advantage of this approach is that the thermal model can be dynamically adjusted depending on the specific usage of the device. As more functions are added to the device, it becomes increasingly important to estimate reaction site temperature based on how the device has been used prior to the bG test.

The mathematical method of the thermal mode relies upon the linear superposition of temperature responses to an applied heat source or sources. A time-varying heat source may be characterized as a series of heat "impulses" of varying magnitude. For the purposes of the present disclosure, an "impulse" is a period of heating lasting a short time as compared to the total duration of heating. Due to linear superposition, the temperature response of a heat source of extended duration can be found by adding up the temperature responses of a succession of impulses that represent that heat source.

Within a device there may be multiple sources of heat, generally caused by the internal heat generation of specific electronic components. Again by linear superposition, the total temperature response of all of these components may be found by summing their individual contributions. These heat sources may become active prior to or during a blood glucose measurement. Their effect on the temperature measurement must be accounted for.

A number of factors affect the temperature response to a given heat source. Within the device enclosure, the heat source may be located on the same circuit board as the temperature sensor or on another circuit board, and it may be near the sensor or far from it. The heat generation of a particular electronic component may vary greatly during its various modes of operation. This heating can be mathematically characterized. The corresponding temperature response at the temperature sensor can also be measured with reasonable accuracy. Depending on the location of the heat producing electronic component relative to the temperature sensor and the nature of the thermal pathways between them, the temperature response at the temperature sensor can vary a great deal. A heat source near the temperature sensor tends to produce a rapid rise in temperature after the heat is applied, followed by a rapid decline in temperature when the heat is removed. For a more distant heat source, the rise and fall in temperature are more gradual and more time elapses before the peak temperature is reached.

The method of linear superposition may be used to characterize the combined effect of multiple, time-varying heat sources in an electronic device, such as a hand-held device incorporating bG measurement circuitry (e.g., the diabetes manager 104). Consider the case of a heat source "A" of strength Qa being applied for duration $(Na/2) \cdot \Delta t$, where Na is an even positive integer and $\Delta t$ is an increment of time. A temperature sensor is installed in the package at a different location than the heat source. Let the temperature elevation at the location of the temperature sensor at time $t_i = i \cdot \Delta t$ after the activation of the heat source be given by $Ea_i = (Ta_i - T_{ref})$ where $Ta_i$ is the temperature at the location of the temperature sensor at time $t_i$, and $T_{ref}$ is a suitable reference temperature.

Let the reference temperature be the ambient temperature of the electronic package: $T_{ref} = T_{amb}$. The temperature elevations $Ea_i$, for times $t_1$ through $t_{Na}$ can be expressed by the following matrix equation:

$$Qa \cdot \begin{bmatrix} 1 & 0 & \ldots & & 0 & 0 & \ldots & & 0 \\ 1 & 1 & 0 & \ldots & 0 & 0 & \ldots & & 0 \\ 1 & 1 & 1 & 0 & \ldots & 0 & 0 & \ldots & 0 \\ \ldots & & & & & \ldots & & & \\ 1 & \ldots & & 1 & 0 & 0 & \ldots & & 0 \\ 1 & 1 & \ldots & & 1 & 0 & \ldots & & 0 \\ 0 & 1 & \ldots & & 1 & 1 & 0 & \ldots & 0 \\ 0 & 0 & 1 & \ldots & 1 & 1 & 1 & 0 & 0 \\ 0 & 0 & 0 & 1 & \ldots & 1 & 1 & 1 & 0 & \ldots & 0 \\ \ldots & & & & & \ldots & & & \\ 0 & \ldots & & & 0 & 1 & 1 & \ldots & 1 & 0 \\ 0 & 0 & \ldots & & & 0 & 1 & 1 & \ldots & 1 \end{bmatrix} \begin{bmatrix} A_1 \\ A_2 \\ \vdots \\ \vdots \\ \vdots \\ \\ \\ \\ \\ \\ A_{Na} \end{bmatrix} =$$

$$\begin{bmatrix} Ea_1 \\ Ea_2 \\ \vdots \\ \vdots \\ \vdots \\ Ea_{Na} \end{bmatrix}$$

or Qa·[U]·[A]=[Ea], where Qa is the magnitude of the heat source at point "A", [U] is the matrix of unit impulses, [A] is the matrix of impulse responses, and [Ea] is the matrix of temperature elevations.

If the magnitude Qa of the heat source and the temperature elevations from times $t_1$ through $t_{Na}$ are known, then the impulse responses $[A_i]$, i=1 to Na, can be determined. Likewise for a heat source at point "B" of strength Qb applied for duration (Nb/2)·Δt, the temperature elevations Ebi for times $t_1$ through $t_{Nb}$ can be expressed by the following matrix equation Qb·[U]·[B]=[Eb], where, Qb is the magnitude of the heat source at point "B", [U] is the matrix of unit impulses, [B] is the matrix of impulse responses, and [Eb] is the matrix of temperature elevations. Similarly, if the magnitude Qb of the heat sources and the temperature elevations from times $t_1$ through $t_{Nb}$ are known, then the impulse responses $[B_i]$, i=1 to Nb, can be found.

To characterize any given heat source "X" among those being considered, the total time duration Nx·Δt should be sufficiently long that for time t>Nx·Δt, the magnitude of the impulse response is approximately zero, i.e., xi≈0 for i>Nx. For the purposes of the thermal model, let Nx be an even number chosen such that either $X_{Nx-1}>0$ and $X_i=0$ for i>Nx−1 or $X_{Nx}>0$ and $X_i=0$ for i>Nx. In other words, $X_i$ is truncated to zero for i>Nx. The interval Δt corresponds to the "impulse" interval, a suitably short interval of time over which a heat source of unit strength acts. The interval Δt should be small compared to the total duration over which the temperature elevations resulting from the applied heat source persist in the body of the electronic device.

For all heat sources of interest, let N be a number equal to the maximum of the individual interval counts Na, Nb, etc.: N≥max {Na, Nb, . . . }. Hence for any given heat source, the impulse response at time ti where i≤N may be zero:

$A_i$≥0 for 1≤i≤Na, $A_i$=0 for i>Na, and Na≤N;

$B_i$≥0 for 1≤i≤Nb, $B_i$=0 for i>Nb, and Nb≤N;

and so on for all heat sources. Thus chosen, the upper limit N on the interval counts will be sufficiently large that the matrix of impulse responses for each and every heat source may be characterized with minimal loss due to truncation.

To characterize the impulse responses of the various heat sources in an electronic device, a series of procedures may be performed, based on the process described above. For each heat source "X" (="A", "B", etc.), the following procedure may be followed:

1) Allow the device to come to equilibrium temperature with its environment. The ambient temperature is the reference temperature: $T_{ref}=T_{amb}$.

2) Activate heat source "X" at constant strength Qx for a duration of (N/2)·Δt, where N and Δt have been chosen in the manner described above (i.e., N≥max {Na, Nb, . . . } and Δt is a suitable impulse interval. Record the initial temperature at the temperature sensor at the time that the heat source is activated and the temperature at each succeeding time $t_i=i·Δt$, i=1 to N/2.

3) At time t=(N/32)·Δt, deactivate the heat source "X" and continue recording the sensor temperature at times $t_i=i·Δt$, i=(N/2)+1 to N.

4) Calculate the temperature elevation at each time step:

$Ex_i=(Tx_i-T_{ref})$, 0≤i≤N

5) Using matrix methods, determine the matrix of impulse temperature responses, [Xi]:

$Qx·[U]·[X]=[Ex]$ $[X]=(1/Qx)·[U]-1·[Ex]$

6) Repeat the above steps for each heat source of interest.

During the procedure, the ambient environment of the electronic device should be held to conditions representative of the environment in which the device is expected to be used. For example, if the device will spend most of its time in still air at room temperature, then these conditions should be maintained. If the operating environment is expected to be drafty, then a suitable airflow should be imposed. Once the impulse response matrices for all of the heat sources have been determined, then the principle of superposition can be applied to determine the expected temperature response of the device to the influence of any combination of these sources acting at arbitrary strengths and for arbitrary durations. The above discussion considered heat sources with constant magnitude.

Consider now a sequence of heat impulses from source k having duration Δt and variable magnitude $[Q_k]$ beginning at time N·Δt before the present:

$[Q_k]=[Q_{k,1}\ Q_{k,2} \ldots Q_{k,N-1}\ Q_{k,N}]$ where the magnitudes of the heat impulses are given by $Q_{k,1}$ is the magnitude at time $t = -N·Δt$ $Q_{k,2}$ is the magnitude at time $t = -(N-1)·Δt$

...

$Q_{k,N-1}$ is the magnitude at time $t = -2·Δt$ $Q_{k,N}$ is the magnitude at time $t = -1·Δt$.

The temperature elevation $E_k$ due to this sequence of impulses from source k is given by $$E_k = \sum_{i=1}^{N} Q_{k,i} \cdot X_{k,N-i+1}$$

or $$E_k = \sum_{i=1}^{N} Q_{k,N-i+1} \cdot X_{k,i}$$

where
$[X_k] = [X_{k,1} \; X_{k,2} \; \ldots \; X_{k,N-1} \; X_{k,N}]$ is the impulse temperature response for source k.

The total temperature elevation due to M sources is given by $$E_{total} = \sum_{k=1}^{M} E_k = \sum_{k=1}^{M} \sum_{i=1}^{N} Q_{k,N-i+1} \cdot X_{k,i}$$

Note that the effect of any temperature impulse prior to time $-N \cdot \Delta t$ is considered negligible and so no corresponding source terms are included in the calculations. This total temperature elevation due to the internal heat sources of the device may now be subtracted from the temperature sensor reading to yield a corrected temperature:

$$T_{corr} = T_{sensor} - E_{total}$$

The customary temperature estimation method may now be applied to this corrected temperature in order to obtain a prediction of the ambient temperature and, hence, the effective test strip reaction site temperature.

To implement the thermal model in a bG measurement device, the control for the device should know which components are being activated and at what strength and for how long. This information plus the reading of the temperature sensor mounted on the circuit board for the bG measurement circuitry is used to determine the temperature response to heat released by each of the heat generating components. Any number of these components may be characterized by the thermal model. The impulse response matrix for each component is stored with the temperature estimation algorithm and may be retrieved to calculate a temperature response whenever that component is activated.

The thermal model contains a number of operating parameters that need to be quantified. The maximum period of time that the temperature response due to an input of heat from any of the components is tracked is given by $N \cdot \Delta t$, where N is the total number of samples and $\Delta t$ is the sampling interval. From the standpoint of the algorithm, N is the total number of elements in the impulse temperature response matrix (dimension N×1) and $\Delta t$ is the impulse duration. For a handheld electronic device (e.g., the diabetes manager 104), this maximum period is on the order of one to two hours. By that time, virtually all of any generated heat will have been dissipated to the environment of the device. The sampling interval $\Delta t$, which is also the assumed impulse duration, should be small enough to resolve the time-varying temperature response from a transient heat release with a sufficient degree of precision that reasonably accurate estimates of the individual and total temperature elevations can be calculated.

For a handheld electronic device such as the diabetes manager 104, a suitable sampling interval might be on the order of several seconds to a few minutes. The exact choice depends on the nature of the heat sources and the degree of precision desired. A sampling interval of one minute appears to provide adequate results for the devices that have been tested. For a maximum tracking period of one hour, a one minute sampling period would yield N=60 samples, and hence 60 elements in the impulse temperature response matrices for the various components. As a further refinement of the thermal model, if the heat being released by a particular component varies during a given sampling period, then the reported strength of that source (which is known by the electronic control) can be adjusted to give a representative average over the interval.

The broad teachings of the disclosure can be implemented in a variety of forms. Therefore, while this disclosure includes particular examples, the scope of the disclosure should not be so limited since other modifications will become apparent to the skilled practitioner upon a study of the drawings, the specification, and the following claims.

What is claimed is:

1. A system for managing power consumption of a handheld diabetes management device and limiting effects of temperature on operations performed by the handheld diabetes management device, the system comprising:
    a temperature sensor that senses an internal temperature of the handheld diabetes management device;
    a port that externally receives a removable measurement strip having a reaction site for receiving a blood sample;
    a thermal modeling module that uses a thermal model to estimate an ambient temperature proximate to the reaction site based on the internal temperature; and
    a power management module that deactivates one or more components of the handheld diabetes management device when the ambient temperature proximate to the reaction site exceeds a threshold temperature,
    wherein the one or more components include;
    a first communication module that communicates with a first device external to the handheld diabetes management device using a first communication protocol, wherein the first device performs a first function associated with a patient, and wherein the first function has a first priority, and
    a second communication module that communicates via a wireless communication link with a second device external to the handheld diabetes management device using a second communication protocol, wherein the second device performs a second function associated with the patient, and wherein the second function has a second priority that is lower than the first priority,
    wherein the power management module deactivates the second communication module before deactivating the first communication module, and
    wherein the first communication module and the second communication module are located within the handheld diabetes management device.

2. The system of claim 1 wherein the first device includes an insulin infusion pump that delivers insulin to the patient, and wherein the second device includes a continuous glucose monitor that monitors glucose level of the patient.

3. The system of claim 1 further comprising:
    a battery that supplies power to the one or more components;
    a fuel gauge module that estimates a remaining capacity of the battery; and
    a temperature sensing module that senses the internal temperature of the handheld diabetes management device,
    wherein the power management module deactivates the one or more components based on the remaining capacity of the battery and the internal temperature of the handheld diabetes management device.

4. The system of claim 1 further comprising a blood glucose measuring module that measures blood glucose in the blood sample and that has accuracy that is characterized over a predetermined temperature range of the reaction site.

5. The system of claim 1 further comprising:
a battery that supplies power to the one or more components; and
a temperature sensing module that senses temperatures at a plurality of locations in the handheld diabetes management device,
wherein the thermal modeling module estimates the ambient temperature and a rate of change of the internal temperature based on the temperatures based on the sensed temperatures and the power supplied to the one or more components, and
wherein the power management module deactivates the one or more components based on the ambient temperature and the rate of change of the internal temperature.

6. The system of claim 1 further comprising a usage monitoring module that monitors usage of the one or more components, wherein the power management module deactivates the one or more components based on the usage of the one or more components of the handheld diabetes management device.

7. The system of claim 1 further comprising:
a usage monitoring module that monitors usage of the one or more components; and
a fuel gauge module that gauges a remaining capacity of a battery that supplies power to the one or more components,
wherein the power management module (i) forecasts remaining operating time of the handheld diabetes management device based on the usage and the remaining capacity of the battery and (ii) deactivates the one or more components based on the forecast.

8. A system for managing power consumption of a handheld medical device and limiting effects of temperature on operations performed by the handheld medical device, the system comprising:
a temperature sensor that senses an internal temperature of the medical device;
a port that externally receives a removable measurement strip having a reaction site for receiving a sample of a substance for measuring a health parameter of a patient;
a thermal modeling module that uses a thermal model to estimate an ambient temperature proximate to the reaction site based on the internal temperature; and
a power management module that deactivates one or more components of the medical device when the ambient temperature proximate to the reaction site is greater than a first threshold temperature or is less than a second threshold temperature,
wherein the one or more components include;
a first communication module that communicates with a first device external to the handheld medical device using a first communication protocol, wherein the first device performs a first function associated with a patient, and wherein the first function has a first priority, and
a second communication module that communicates via a wireless communication link with a second device external to the handheld medical device using a second corn communication protocol, wherein the second device performs a second function associated with the patient, and wherein the second function has a second priority that is lower than the first priority,
wherein the power management module deactivates the second communication module before deactivating the first communication module, and
wherein the first communication module and the second communication module are located within the handheld medical device.

9. The system of claim 8 wherein the first device includes an insulin infusion pump that delivers insulin to the patient, and wherein the second device includes a continuous glucose monitor that monitors glucose level of the patient.

10. The system of claim 8 further comprising:
a battery that supplies power to the one or more components;
a fuel gauge module that estimates a remaining capacity of the battery; and
a temperature sensing module that senses the internal temperature of the handheld medical device,
wherein the power management module deactivates the one or more components based on the remaining capacity of the battery and the internal temperature of the handheld medical device.

11. The system of claim 8 further comprising a blood glucose measuring module that has accuracy that is characterized over a predetermined temperature range of the reaction site.

12. The system of claim 8 further comprising:
a battery that supplies power to the one or more components; and
a temperature sensing module that senses temperatures at a plurality of locations in the handheld medical device based on power supplied to the one or more components,
wherein the thermal modeling module estimates the ambient temperature and a rate of change of the internal temperature based on the temperatures, and
wherein the power management module deactivates the one or more components based on the ambient temperature and the rate of change of the internal temperature.

13. The system of claim 8 further comprising:
a battery that supplies power to the one or more components; and
a glucose measuring module that measures an amount of the substance in the sample.

14. The system of claim 8 further comprising a usage monitoring module that monitors usage of the one or more components, wherein the power management module deactivates the one or more components based on the usage of the one or more components of the handheld medical device.

15. The system of claim 8 further comprising:
a usage monitoring module that monitors usage of the one or more components; and
a fuel gauge module that gauges a remaining capacity of a battery that supplies power to the one or more components,
wherein the power management module (i) forecasts remaining operating time of the handheld medical device based on the usage and the remaining capacity of the battery and (ii) deactivates the one or more components based on the forecast.

* * * * *